(12) United States Patent
Day

(10) Patent No.: US 7,918,776 B2
(45) Date of Patent: Apr. 5, 2011

(54) COMPOSITION FOR DISPOSING OF UNUSED MEDICINES

(76) Inventor: Sherry Day, Poynette, WI (US)

( * ) Notice: Subject to any disclaimer, the term of this patent is extended or adjusted under 35 U.S.C. 154(b) by 712 days.

(21) Appl. No.: 11/942,471

(22) Filed: Nov. 19, 2007

(65) Prior Publication Data

US 2009/0131732 A1    May 21, 2009

(51) Int. Cl.
  *B09B 1/00* (2006.01)
  *B09B 3/00* (2006.01)
  *B09B 5/00* (2006.01)
  *C21B 3/06* (2006.01)

(52) U.S. Cl. ............... 588/249.5; 588/251; 588/900

(58) Field of Classification Search .......... 134/140, 134/18, 22.18, 116, 156, 153, 155, 157, 159; 210/610, 664; 232/43.1, 16, 41; 703/2, 4, 703/31; 588/249.5, 900
See application file for complete search history.

(56) References Cited

U.S. PATENT DOCUMENTS

| | | | |
|---|---|---|---|
| 4,415,451 A | 11/1983 | Suzuki | |
| 4,919,569 A | 4/1990 | Wittenzelliner | |
| 5,277,869 A | 1/1994 | Glazer et al. | |
| 5,348,235 A | 9/1994 | Pappas | |
| 5,427,737 A | 6/1995 | Glazer et al. | |
| 5,547,582 A | 8/1996 | Waibel | |
| 5,568,895 A | 10/1996 | Webb et al. | |
| 5,582,793 A | 12/1996 | Glazer et al. | |
| 5,776,260 A | 7/1998 | Dunn et al. | |
| 5,957,372 A | 9/1999 | Dean et al. | |
| 5,961,036 A | 10/1999 | Michael et al. | |
| 5,972,291 A | 10/1999 | Healy et al. | |
| 6,263,887 B1 | 7/2001 | Dunn | |
| 6,588,436 B2 | 7/2003 | Dunn et al. | |
| 6,776,175 B2 | 8/2004 | Dunn et al. | |
| 6,868,344 B1 | 3/2005 | Nelson | |
| 7,184,897 B2 | 2/2007 | Nelson | |
| 2005/0096941 A1 | 5/2005 | Tong | |
| 2005/0267784 A1 | 12/2005 | Slen | |

OTHER PUBLICATIONS

"Odor" publication by Utah State University (Jan. 15, 2006).*
"Skunks" publication by NC State University (Aug. 23, 2004).*
"Adsorption" publication by Lenntech (Dec. 21, 2005).*
"Home Remedies for Skunk Odors" Rutherford County, Feb. 1, 2001.*

* cited by examiner

*Primary Examiner* — J. A. Lorengo
*Assistant Examiner* — Jennifer A Smith
(74) *Attorney, Agent, or Firm* — Absolute Technology Law Group, LLC

(57) ABSTRACT

A composition for destruction of unused or expired medicines comprised of: an acidic solvent; a dishwashing liquid; and activated carbon. The acidic solvent can be distilled vinegar, lemon juice, hydrochloric acid, diluted hydrochloric acid, acetic acid, diluted acetic acid, bleach, ammonia, alcohol, and combinations thereof, the dishwashing liquid includes at least one anionic surfactant, at least one nonionic surfactant, and cocinin, and the activated carbon is selected can be powdered activated carbon or granulated activated carbon, typically with a surface area of at least approximately 500 square meters per gram. The composition can further include fragrance and/or coloring. The components of the composition can also be sold individually or one or more components can be sold together with a container.

15 Claims, No Drawings

COMPOSITION FOR DISPOSING OF UNUSED MEDICINES

FIELD OF INVENTION

This invention relates generally to the field of medical waste, and specifically to a composition for disposing of unused medicines.

BACKGROUND

There is currently no effective widely used way to dispose of unused, expired, or confiscated medicines, i.e., pharmaceuticals and personal care products (PPCPs), whether by individuals disposing of personal medicines or medical facilities disposing of larger amounts of unused medicines. Medicines are oftentimes simply thrown into the trash. Children or animals may find and ingest medicines that are simply tossed into the trash and once they reach the landfill they can seep into the ground water.

One method commonly used is to add bleach to the PPCPs to dissolve them, add kitty litter to the mixture, and then place the mixture in to the garbage. Drawbacks of this method include the inability to effectively dissolve the PPCPs, emission of noxious fumes, and if the entity destroying the PPCPs is a medical facility, the need to have large quantities of these items on hand.

Another technique is to dissolve the PPCPs in water and then add some type of flour or spice to make a pungent and unsightly mixture to discourage anyone from eating it or using it for an illegal purpose of sale or consumption. Unfortunately, many PPCPs are not readily dissolved in water, and for those wanting the mixture for illegal sale or consumption, this technique does not deter the criminal.

It is also common to attempt to dispose of the PPCPs by wrapping the unused portion in duct tape to conceal its contents and make it difficult to extract the PPCPs from the tape. However, this does not deter those wanting the PPCPs for illegal purposes.

Medication take-back programs are sometimes used, but such programs require extensive planning by communities and as such are held only once or twice a year. In addition, due to the extent of planning, broadcasting dates of the event, and the need for a law enforcement officer present to take custody of the controlled substances, such programs are often cost-prohibitive. In addition, there is no requirement that pharmacists take back unused or expired medications or that they are disposed of in any particular manner, resulting in an ad hoc practice.

At hospitals and other medical facilities, disposing of medications requires extensive training of all staff working with the unused and/or discarded medications, the medications must be sorted into separate containers, a designated locked disposal area must be provided, security personnel are needed to move the medications through the facility to the disposal area, the medications must be sent to a special disposal facility for destruction, and records must be kept and reported to negate the possibility of the medications being lost or stolen for illegal use.

The most common method for disposing of unused PPCPs is to simply dispose of them down the drain or toilet and into the sewer system. However, this results in the introduction of pharmaceutical residuals into the world's aquatic environments. Most septic systems don't destroy the PPCPs. On the contrary, they may destroy the bacteria in the septic system that aid in breaking down the waste in the household waste water. In addition, because most waste water treatment plants are not designed to remove or destroy PPCPs from waste water in the sewage system, the PPCPs may be discharged into lakes, rivers, or oceans.

According to the U.S. Geological Survey, concentrations of pharmaceutically active compounds, such as hormones (including steroids and birth control pills), antidepressants, antibiotics and antimicrobials, and chemicals from personal care products have been found in various waterways nationwide. The two largest sources of pharmaceuticals entering the sewer systems are from medical facilities (including hospitals, nursing facilities, and veterinary hospitals) and residents.

What is needed is an effective method of destroying and/or disposing of unused or expired medications. Such a method will reduce the potential for environmental impacts, reduce the amount of medication available for potential abuse or accidental ingestion, and prevent inadvertent use of expired medications.

As used herein, the terms "medicine," "medicines," "medication," "medications," and "pharmaceuticals and personal care products" (PPCPs) refer to any agent, drug, or curative substance used in treating, preventing, or alleviating the symptoms of a disease, illness, condition, or injury and shall be collectively referred to herein as "medicines." Such medicines can be in any form, including tablets, capsules, liquids, syrups, creams, lozenges, lollipops, ointments, powders, patches, suppositories, and combinations thereof.

DETAILED DESCRIPTION OF EMBODIMENTS OF THE INVENTION

For the purpose of promoting an understanding of the present invention, references are made in the text hereof to embodiments of a composition for disposing of unused medicines and methods of using same, only some of which are described herein. It should nevertheless be understood that no limitations on the scope of the invention are thereby intended. One of ordinary skill in the art will readily appreciate that modifications such as the exact amount of the components, alternate but functionally similar materials from which the composition is made, and the inclusion of additional constituent are deemed readily apparent and obvious to one of ordinary skill in the art, and all equivalent relationships to those described in the written description do not depart from the spirit and scope of the present invention. Some of these possible modifications are mentioned in the following description. Therefore, specific details disclosed herein are not to be interpreted as limiting, but rather as a basis for the claims and as a representative basis for teaching one of ordinary skill in the art to employ the present invention in virtually any appropriately detailed apparatus or manner.

Moreover, the term "substantially" or "approximately" as used herein may be applied to modify any quantitative representation that could permissibly vary without resulting in a change in the basic function to which it is related. For example, one embodiment of the composition for disposing of unused medicines is disclosed herein as including distilled vinegar having approximately five percent acetic acid. The proportion of acetic acid may be less than this value and still be within the scope of the invention if its functionality is not materially altered.

The composition of the instant invention is comprised of three (3) components that break down and destroys narcotics and other medicines to prevent their diversion for illegal sale or consumption. The combination includes: distilled vinegar, dishwashing liquid, and activated carbon.

Distilled vinegar has roughly the same acidity (a pH of about 2.4) as the human body's gastric juices (a pH of about 1.0) in which the medications are designed to dissolve, whether quickly or over time. Thus, placing unused, expired, or otherwise unwanted medicines in distilled vinegar will break down most medicines within about 15 minutes. In other embodiments, the medicines can be break down in lemon juice (which has a pH of about 2.2), hydrochloric acid (a pH of about 0.0), diluted hydrochloric acid, acetic acid, diluted acetic acid, bleach, ammonia, alcohol, and combinations thereof, herein referred to as an acidic solvent. However, lemon juice does not increase the break down process and is more costly; hydrochloric acid is very corrosive and requires additional precautions because of its high acidity; and bleach, ammonia, and alcohol increase the likelihood of toxic fumes and/or toxic and/or chemical reactions occurring. Because distilled vinegar is inexpensive, readily available, and relatively innocuous, the preferred embodiment of the invention includes distilled vinegar. The distilled vinegar should have at least five prevent (5%) acetic acid content. If not, additional distilled vinegar may be required.

The inclusion of dishwashing liquid reduces the time required to break down the medicines to between approximately five (5) to ten (10) minutes. Some medications are made specifically to break down slower when ingested, to provide an extended release of the medicine. The addition of surfactants speeds the break down process by penetrating the tablets or capsules Dishwashing liquid, generic or otherwise, is defined as any substance containing at least one (1) anionic surfactant, at least one (1) nonionic surfactant, and cocinin. Dishwashing liquid is also inexpensive, readily available, and innocuous, and therefore does not require any special handling. In addition, dishwashing liquid is an effective substitute for ipecac syrup (used to induce vomiting). Penetration of the dishwashing liquid in to the medicines to be destroyed thus further acts as an additional deterrent to anyone trying to divert them illegally.

The resulting mixture, i.e., the medicine, the distilled vinegar or other acidic solvent and dishwashing liquid, can still cause environmental effects if disposed of directly into a sink, toilet, or otherwise in to a wastewater system. In order to minimize this risk, activated carbon is used, either powdered activated carbon (PAC) or granulated activated carbon (GAC). The PAC or GAC effectively binds with the active ingredients of the medicine. Activated carbon can have a surface area in excess of five hundred square meters per gram (500 $m^2/g$), with one thousand five hundred square meters per gram (1,500 $m^2/g$) being readily achievable. Examples of an acceptable activated carbon include GAC 8/20, 12/40, and 8/30. Activated carbon has an affinity for adsorption of the active ingredients of the medicines, but does not have an affinity for the acetic acid of the distilled vinegar or acidic component of the other acidic solvents provided supra or the dishwashing liquid. Binding the active components of the dissolved medicines to the AC thus provides a stable compound for storage and delivery of the dissolved medicines.

To compliment the environment, in one embodiment, the components of the instant invention can be contained in a waxed cardboard container, similar to a milk carton. In one (1) embodiment, the container includes an opening approximately two inches (2") wide. A screw type lid or a child proof lid can be further included. In one (1) embodiment, the container is capable of holding approximately twenty ounces (20 oz.) of material. In such an embodiment, approximately three ounces (3 oz.) of granulated activated carbon is added to the wax coated container along with approximately four ounces (4 oz.) generic dishwashing liquid and approximately six ounces (6 oz.) of distilled vinegar having at least five percent (5%) acetic acid. This leaves a six ounce (6 oz.) capacity for medicines to be added for disposal and approximately one ounce (1 oz.) for proper mixing of discarded medicines.

The exact amount of each component needed, however, will depend on the amount of medicine(s) to be destroyed. That is, for every ounce of medicine(s) to be destroyed, this embodiment uses one half ounce (½ oz.) activated carbon, two-thirds of an ounce (⅔ oz.) dishwashing liquid, and one ounce (1 oz.) of distilled vinegar. The container can similarly be sized to accommodate greater or lesser volumes of the composition, the medicine(s) to be destroyed, and space for mixing.

These values, however, are only one (1) embodiment. In other embodiments of the composition, for every ounce of medicine(s) to be destroyed, a minimum of approximately one-sixth of an ounce (⅙ oz.) activated carbon, approximately one-half ounce (½ oz.) of dishwashing liquid, and approximately two-thirds of an ounce (⅔ oz.) of distilled vinegar (or other acidic solvent) should be used. Maximum volumes necessary for proper destruction of each ounce of the medicine(s) are approximately one half ounce (½ oz.) activated carbon, approximately two-thirds of an ounce (⅔ oz.) distilled vinegar or other acidic solvent, and approximately one ounce (1 oz.) of distilled vinegar.

In use, the container is then shaken vigorously for one (1) minute, the lid or opening closed, and the container discarded. Because the components break down into environmentally inert materials, the container can be placed into an ordinary refuse system. The use of a paper-based container minimizes the adverse environmental impact, though other types of containers can be used, including plastic and metal.

In another embodiment, a container can be manufactured and the activated carbon added. The container with AC contained within can then be sold. The individual wanting to destroy the medicines can then add distilled vinegar (or other acidic solvent) and the dishwashing liquid, both inexpensive and readily available. The container is then ready to accept the medicines for destruction. Such an apparatus can further include fill lines so that the user does not have to measure the other components.

In still another embodiment, the container can be manufactured and sold with the AC already contained within it, as above, but also already further including the distilled vinegar (or other acidic solvent) and the dishwashing liquid also contained within in pre-determined quantities. Such a container can also further include fill lines so that the user does not have to measure the other components.

The composition can further include a coloring and/or a fragrance. Coloring should be environmentally friendly, but can be natural or artificial, and addition of a fragrance, such as apple or citrus, would help to cover up the strong vinegar or acetic acid smell.

Such a composition, whether purchased as individual components or as a pre-prepared container having the components and space in which to add the medicines to be destroyed, has several applications. It can be used for personal home use by individuals to discard unused and/or expired medicines, by in-home care givers such as Hospice and Home Health Providers, and in commercial uses such as hospitals, long-term care facilities, medical clinics, and veterinary offices.

While the composition for disposing of unused medicines has been shown and described with respect to several embodiments and uses in accordance with the present invention, it is to be understood that the same is not limited thereto, but is susceptible to numerous changes and modifications as known to a person of ordinary skill in the art, and it is intended that the present invention not be limited to the details shown and described herein, but rather cover all such changes and modifications obvious to one of ordinary skill in the art.

What is claimed is:

1. A composition comprised of:
    an acidic solvent to dissolve and break down medicines;
    a dishwashing liquid of a composition capable of acting as an effective substitute for ipecac syrup to induce vomiting; and
    activated carbon;
    wherein said acidic solvent, said dishwashing liquid capable of acting as an effective substitute for ipecac syrup and said activated carbon are combined in a ratio of two-thirds to one ounce of said acidic solvent, one-half to two-thirds of an ounce of said dishwashing liquid of a composition capable of acting as an effective substitute for ipecac syrup to induce vomiting, and one-sixth to one-half of an ounce of said activated carbon for every one ounce of medicines; and
    wherein said chemical composition is used to render one or more medicines unfit for consumption.

2. The composition of claim 1, wherein said acidic solvent is selected from a group consisting of distilled vinegar, lemon juice, hydrochloric acid, diluted hydrochloric acid, acetic acid, diluted acetic acid, bleach, ammonia, alcohol, and combinations thereof.

3. The composition of claim 1, wherein said acidic solvent includes at least approximately five percent acetic acid.

4. The composition of claim 1, wherein said activated carbon is selected from a group consisting of powdered activated carbon or granulated activated carbon.

5. The composition of claim 1, wherein said activated carbon has a surface area of at least approximately 500 square meters per gram.

6. The composition of claim 1, wherein said chemical composition further includes at least one additional constituent selected from a group consisting of a fragrance and a color.

7. A composition for destroying at least one medicine comprised of:
    an acidic solvent to dissolve and break down medicines, said acidic solvent including at least approximately five percent acetic acid;
    a dishwashing liquid of a composition capable of acting as an effective substitute for ipecac syrup to induce vomiting, said dishwashing liquid of a composition capable of acting as an effective substitute for ipecac syrup to induce vomiting including at least one anionic surfactant, at least one nonionic surfactant, and cocinin; and
    activated carbon, said activated carbon having a surface area of at least approximately 500 square meters per gram;
    wherein said acidic solvent, said dishwashing liquid capable of acting as an effective substitute for ipecac syrup and said activated carbon are combined in a ratio of two-thirds to one ounce of said acidic solvent, one-half to two-thirds of an ounce of said dishwashing liquid of a composition capable of acting as an effective substitute for ipecac syrup to induce vomiting, and one-sixth to one-half of an ounce of said activated carbon for every one ounce of medicines.

8. The composition of claim 7, wherein said acidic solvent is selected from a group consisting of distilled vinegar, lemon juice, hydrochloric acid, diluted hydrochloric acid, acetic acid, diluted acetic acid, bleach, ammonia, alcohol, and combinations thereof.

9. The composition of claim 7, wherein said activated carbon is selected from a group consisting of powdered activated carbon or granulated activated carbon.

10. The composition of claim 7, wherein said chemical composition further includes at least one additional constituent selected from a group consisting of a fragrance and a color.

11. A composition for rendering one or more medicines unfit for consumption comprised of:
    distilled vinegar to dissolve and break down medicines;
    a dishwashing liquid of a composition capable of acting as an effective substitute for ipecac syrup to induce vomiting; and
    activated carbon;
    wherein said distilled vinegar, said dishwashing liquid capable of acting as an effective substitute for ipecac syrup and said activated carbon are combined in a ratio of two-thirds to one ounce of said distilled vinegar, one-half to two-thirds of an ounce of said dishwashing liquid of a composition capable of acting as an effective substitute for ipecac syrup to induce vomiting, and one-sixth to one-half of an ounce of said activated carbon for every one ounce of medicines.

12. The composition of claim 11, wherein said acidic solvent includes at least approximately five percent acetic acid.

13. The composition of claim 11, wherein said activated carbon is selected from a group consisting of powdered activated carbon or granulated activated carbon.

14. The composition of claim 11, wherein said activated carbon has a surface area of at least approximately 500 square meters per gram.

15. The composition of claim 11, wherein said chemical composition further includes at least one additional constituent selected from a group consisting of a fragrance and a color.

* * * * *